United States Patent
Ewers et al.

(10) Patent No.: US 6,837,847 B2
(45) Date of Patent: Jan. 4, 2005

(54) SHAPE LOCKABLE APPARATUS AND METHOD FOR ADVANCING AN INSTRUMENT THROUGH UNSUPPORTED ANATOMY

(75) Inventors: Richard C. Ewers, Fullerton, CA (US); Vahid Saadat, Saratoga, CA (US); Eugene G. Chen, Carlsbad, CA (US)

(73) Assignee: USGI Medical, Inc., San Clemente, CA (US)

( * ) Notice: Subject to any disclaimer, the term of this patent is extended or adjusted under 35 U.S.C. 154(b) by 129 days.

(21) Appl. No.: 10/173,238

(22) Filed: Jun. 13, 2002

(65) Prior Publication Data

US 2003/0233027 A1 Dec. 18, 2003

(51) Int. Cl.[7] .................................................. A61B 1/04
(52) U.S. Cl. ........................ 600/114; 600/121; 600/127
(58) Field of Search .............................. 600/114, 115, 600/117, 110, 121, 127, 129, 139, 140, 141, 142, 143, 144, 146, 150, 151

(56) References Cited

U.S. PATENT DOCUMENTS

| | | | |
|---|---|---|---|
| 4,176,662 A | | 12/1979 | Frazer |
| 4,577,621 A | * | 3/1986 | Patel .......................... 600/114 |
| 4,601,283 A | | 7/1986 | Chikama |
| 4,624,243 A | * | 11/1986 | Lowery et al. ............. 600/136 |
| 4,646,722 A | | 3/1987 | Silverstein et al. |
| 4,815,450 A | | 3/1989 | Patel |
| 5,092,901 A | | 3/1992 | Hunter et al. |
| 5,174,276 A | | 12/1992 | Crockard |
| 5,217,001 A | | 6/1993 | Nakao et al. |
| 5,251,611 A | * | 10/1993 | Zehel et al. ................ 600/141 |
| 5,325,845 A | * | 7/1994 | Adair .......................... 600/114 |
| 5,337,733 A | | 8/1994 | Bauerfeind et al. |
| 5,402,768 A | * | 4/1995 | Adair .......................... 600/106 |
| 5,429,118 A | * | 7/1995 | Cole et al. .................. 600/121 |
| 5,620,408 A | * | 4/1997 | Vennes et al. .............. 600/114 |
| 5,759,151 A | * | 6/1998 | Sturges ....................... 600/146 |
| 5,779,624 A | | 7/1998 | Chang |
| 5,807,241 A | * | 9/1998 | Heimberger ................ 600/142 |
| 5,842,973 A | * | 12/1998 | Bullard ....................... 600/194 |
| 6,099,464 A | * | 8/2000 | Shimizu et al. ............. 600/104 |
| 6,174,280 B1 | * | 1/2001 | Oneda et al. ............... 600/121 |
| 6,179,776 B1 | | 1/2001 | Adams et al. |
| 6,306,081 B1 | * | 10/2001 | Ishikawa et al. ............ 600/127 |
| 6,315,714 B1 | | 11/2001 | Akiba |
| 2002/0022765 A1 | | 2/2002 | Belson |
| 2002/0062062 A1 | | 5/2002 | Belson et al. |
| 2002/0120178 A1 | | 8/2002 | Tartaglia et al. |
| 2002/0147385 A1 | | 10/2002 | Butler et al. |
| 2002/0161281 A1 | | 10/2002 | Jaffe et al. |

FOREIGN PATENT DOCUMENTS

DE 28 23 025 12/1979

* cited by examiner

*Primary Examiner*—Beverly M. Flanagan
(74) *Attorney, Agent, or Firm*—Townsend and Townsend and Crew LLP

(57) ABSTRACT

Apparatus and methods are provided for placing and advancing a diagnostic or therapeutic instrument in a hollow body organ of a tortuous or unsupported anatomy, comprising a handle, an overtube, a distal region having an atraumatic tip. The overtube may be removable from the handle, and have a longitudinal axis disposed at an angle relative to the handle. The overtube may be selectively stiffened to reduce distension of the organ caused by advancement of the diagnostic or therapeutic instrument. The distal region permits passive steering of the overtube caused by deflection of the diagnostic or therapeutic instrument while the atraumatic tip prevents the wall of the organ from becoming caught or pinched during manipulation of the diagnostic or therapeutic instrument.

32 Claims, 16 Drawing Sheets

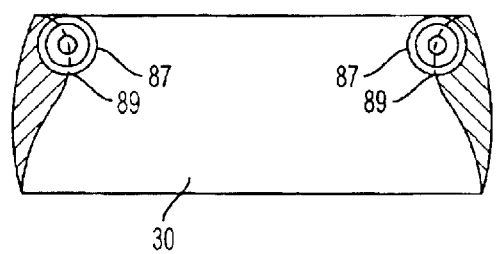 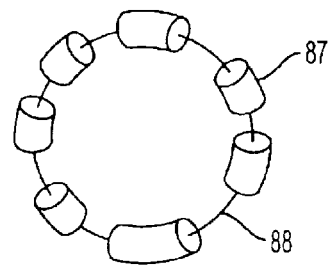
FIG. 10A                FIG. 10B
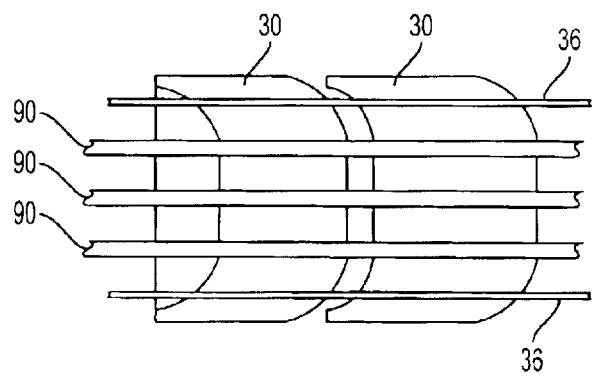 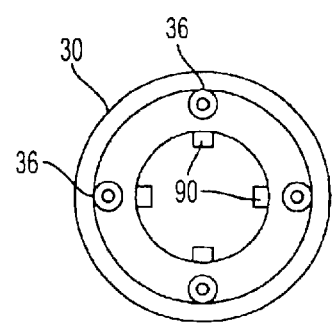
FIG. 11A                FIG. 11B

SHAPE LOCKABLE APPARATUS AND METHOD FOR ADVANCING AN INSTRUMENT THROUGH UNSUPPORTED ANATOMY

FIELD OF THE INVENTION

The present invention relates to apparatus and methods for placing and advancing a diagnostic or therapeutic instrument in a hollow body organ of unsupported anatomy, while reducing patient discomfort and risk of injury.

BACKGROUND OF THE INVENTION

The use of the colonoscope for examining the interior of the large intestine or colon is well-known. In general, a physician performing an examination or treatment of the colon inserts a colonoscope into the anus and then advances the colonoscope into the colon. A complete examination requires the physician to advance the colonoscope into the colon, negotiate the sigmoid colon, and left and right colic flexures up to the cecum. Advancement of the colonoscope is generally accomplished by manipulation of a steerable tip of the colonoscope, which is controlled at the proximal end of the device by the physician, in addition to torquing and pushing the scope forward or pulling it backward.

Problems regularly occur, however, when negotiating the colonoscope through the bends of the colon, such as at the sigmoid and left and right colic flexures. These problems arise because the colon is soft and has unpredictable fixation points to the viscera of the abdomen, and it is easily distensible. Consequently, after the steerable tip of the colonoscope is deflected to enter a new region of the colon, the principal direction of the force applied by the physician urging the proximal end of the device into the patient's colon is not in the direction of the steerable tip. Instead, the force is directed along the axis of the colonoscope towards the preceding bend(s), and causes yielding or displacement of the colon wall.

The loads imposed by the colonoscope on the colon wall can have a myriad of possible effects, ranging from patient discomfort to spastic cramp-like contractions of the colon and even possible perforation or dissection of the colon. Consequently, the colonoscope cannot be advanced as far as the cecum in up to one-sixth of all cases.

To address some of these difficulties, it is known to employ a guide tube that permits a colonoscope to be advanced through the rectum. One such device is described in U.S. Pat. No. 5,779,624 to Chang. An alternative approach calls for inserting the colonoscope through a curved region, and then mechanically actuating the portion of the device in the curved region to cause it to straighten, as described in U.S. Pat. No. 4,601,283 to Chikama.

Many patients find the operation of such previously-known devices unpleasant because the sigmoid portion of the colon is forced into an almost rectilinear shape by the guide tube. Due to the stiffness of the guide tube, careless handling of the guide tube presents a risk of injury to the colon.

Other previously-known apparatus and methods use an overtube having variable rigidity, so that the overtube may be inserted through curved anatomy in a flexible state, and then selectively stiffened to resist bending forces generated by passing a colonoscope through the overtube. One example of such a device is described in U.S. Pat. No. 5,337,733 to Bauerfiend. The device described in that patent comprises inner and outer walls having opposing ribs spaced apart across an air-filled annulus. The ribs are selectively drawn together to intermesh, and form a rigid structure by evacuating the annulus.

Another previously-known endoscopic device for delivering aneurysm clips within a hollow organ or vessel is described in U.S. Pat. No. 5,174,276 to Crockard. The device described in that patent includes a conduit formed from a multiplicity of elements that are capable of angulation relative to one another, and which becomes rigid when subjected to a tensile force. The device is described as being particularly useful in neurosurgery, where the variable rigidity of the device is useful for providing a stable platform for neurosurgical interventions, such as clipping an aneurysm.

While previously-known apparatus and methods provide some suggestions for solving the difficulties encountered in advancing diagnostic or therapeutic instruments through easily distensible body organs, few devices are commercially available. Although the precise reasons for this lack of success are uncertain, previously-known devices appear to pose several problems.

For example, the devices described in the Bauerfiend and Crockard patents appear to pose a risk of capturing or pinching tissue between the endoscope/colonoscope and the distal end of the overtube or conduit when the scope is translated. Also, neither device provides any degree of steerability, and must be advanced along the pre-positioned scope. In addition, the bulk of the proximal tensioning system described in Crockard is expected to interfere with manipulation of the endoscope. Other drawbacks of previously-known devices may be related to the complexity or cost of such devices or the lack of suitable materials. In any event, there exists an un-met need for devices to solve this long-felt problem in the field of endoscopy and colonoscopy.

In view of the foregoing, it would be desirable to provide apparatus and methods for facilitating placement of diagnostic or therapeutic instruments within easily distensible hollow body organs, such as the esophagus or colon.

It further would be desirable to provide apparatus and methods that permit a diagnostic or therapeutic device to be advanced into a hollow body organ, and which facilitates passage of the device through tortuous anatomy without requiring straightening of organ passageways already traversed.

It also would be desirable to provide apparatus and methods for facilitating placement of diagnostic or therapeutic instruments within easily distensible hollow body organs that include means for reducing the risk that tissue will become inadvertently pinched between the sheath apparatus and the advancing or withdrawing instrument, or caught as the diagnostic or therapeutic instrument is maneuvered through the hollow body organ.

It still further would be desirable to provide apparatus and methods that provide a low-cost, single use, easily manufacturable guide for inserting a diagnostic or therapeutic instrument in a hollow body organ.

It yet further would be desirable to provide apparatus and methods that provide a low-cost, easily manufacturable guide for inserting a diagnostic or therapeutic instrument in a hollow body organ, wherein a portion of the apparatus is disposable after a single use and a remaining portion of the device is re-usable.

Still further, it would be desirable to provide a device having a selectively locking shape for inserting a diagnostic or therapeutic instrument in a hollow body organ, but which facilitates manipulation of a proximal end of the diagnostic or therapeutic instrument.

It additionally would be desirable to permit multiple diagnostic or therapeutic devices to be positioned in a hollow, unsupported organ, so that at least one of the devices may be withdrawn and repositioned while the other devices are retained in place.

SUMMARY OF THE INVENTION

In view of the foregoing, it is an object of the present invention to provide apparatus and methods for facilitating placement of diagnostic or therapeutic instruments within easily distensible or unpredictably supported hollow body organs, such as the esophagus or colon.

It is a further object of the present invention to provide apparatus and methods that permit a diagnostic or therapeutic device to be advanced into a hollow body organ, and which facilitates passage of the device through tortuous anatomy without requiring straightening of organ passageways already traversed.

It also is an object of the present invention to provide apparatus and methods for facilitating placement of diagnostic or therapeutic instruments within easily distensible hollow body organs that include means for reducing the risk that tissue will become inadvertently pinched or caught as the diagnostic or therapeutic instrument is maneuvered through the hollow body organ.

It is a still further object of the present invention to provide apparatus and methods that provide a low-cost, single use, easily manufacturable guide for inserting a diagnostic or therapeutic instrument in a hollow body organ.

It is another object of this invention to provide apparatus and methods that provide a low-cost, easily manufacturable guide for inserting a diagnostic or therapeutic instrument in a hollow body organ wherein a portion of the apparatus is disposable after a single use and a remaining portion of the device is re-usable.

Still further, it is an object of the present invention to provide a device having a selectively locking shape for inserting a diagnostic or therapeutic instrument in a hollow body organ, but which facilitates manipulation of a proximal end of the diagnostic or therapeutic instrument.

It is yet another object of the present invention to permit multiple diagnostic or therapeutic devices to be positioned in a hollow, unsupported organ, so that at least one of the devices may be withdrawn and repositioned while the other devices are retained in place.

These and other objects of the present invention are attained by providing apparatus comprising a proximal handle, an overtube coupled to the proximal handle and having a distal region, and an atraumatic tip disposed on the distal region. The apparatus includes a main lumen extending between the handle, overtube and atraumatic tip, through which a diagnostic or therapeutic instrument, such as an endoscope or colonoscope, may be translated.

The handle extends from the patient, e.g., through the mouth or anus, where it can be manipulated by the physician. The handle preferably comprises means for selectively locking the shape of the overtube. In this manner the overtube may be shape locked to assist one or more diagnostic or therapeutic instruments to negotiate the tortuous or unsupported anatomy of a hollow body organ, rather than distending the wall of the organ. The proximal handle may form part of a single use, disposable apparatus, or may be separable from the overtube and reusable. The overtube preferably is angled relative to a working axis of the handle, so that the handle does not interfere with manipulation of the diagnostic or therapeutic instrument inserted through the overtube.

An overtube constructed in accordance with the principles of the present invention may comprise a multiplicity of selectively-tensionable nested elements, a series of interconnected links surrounded by a selectively actuable clamping mechanism, a tubular member comprising a multiplicity of helical links formed from a material having variable durometer and surrounded by a clamping mechanism, or a thermoresponsive polymer or alloy. The overtube may include any of a number of aids for facilitating passage of the diagnostic or therapeutic instrument through the main lumen, including a lubricious liner, rails or rollers.

The atraumatic tip of the present invention preferably is configured to reduce the risk of capturing or pinching tissue between the overtube and a diagnostic or therapeutic instrument that is selectively translated through the overtube. This is preferably accomplished by the atraumatic tip applying a radially-outwardly directed load to the wall of the hollow body organ in the vicinity of the distal region where the diagnostic or therapeutic instrument exits the apparatus.

In addition, the distal region of the overtube preferably includes a flexible portion that permits a steerable tip of a diagnostic or therapeutic device disposed within the distal region to deflect the distal region of the overtube in a desired direction. This permits the overtube to be readily advanced together with the steerable tip of the diagnostic or therapeutic device.

BRIEF DESCRIPTION OF THE DRAWINGS

Further features of the invention, its nature and various advantages will be more apparent from the accompanying drawings and the following detailed description of the preferred embodiments, in which:

FIGS. 10A and 10B, are a side-section view of an alternative element suitable for use in the overtube of FIG. 2 and a roller element suitable for use with the element of FIG. 10A, respectively;

FIGS. 11A and 11B depict the use of lubricious rails in the overtube of the apparatus of FIG. 2 or 9 to facilitate passage of a diagnostic or therapeutic device through the main lumen;

DETAILED DESCRIPTION OF THE INVENTION

Figure 1:
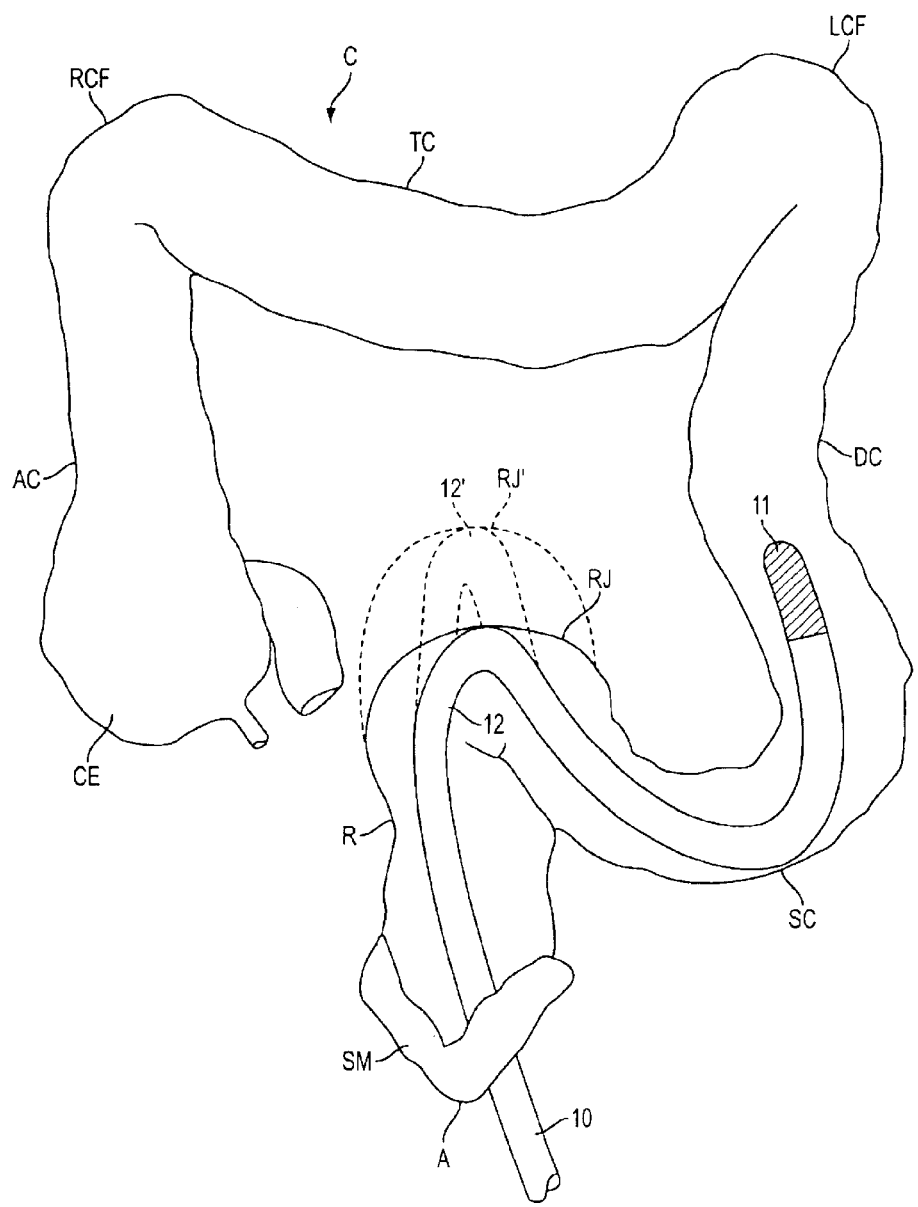
FIG. 1 is a schematic view of a human colon illustrating a common difficulty encountered in advancing a colonoscope beyond the sigmoid colon.

Referring to FIG. 1, problems associated with previously-known apparatus and methods for inserting and advancing a diagnostic or therapeutic instrument into a hollow body organ having tortuous or unsupported anatomy, illustratively, patient's colon C, are described. Colon C includes sphincter muscle SM disposed between anus A and rectum R. Rectum R is coupled via the rectosigmoid junction RJ to sigmoid colon SC. Sigmoid colon SC joins descending colon DC, which in turn is coupled to transverse colon TC via left colic flexure LCF. Transverse colon TC also is coupled by right colic flexure RCF to ascending colon AC and cecum CE, which receives waste products from the small intestine.

As illustrated in FIG. 1, colonoscope 10 having steerable distal tip 11 is typically inserted through anus A into rectum R, and then steered through rectosigmoid junction RJ into sigmoid colon SC. As depicted in FIG. 1, distal tip 11 of colonoscope 10 is advanced through sigmoid colon SC and deflected into descending colon DC. Further urging of the colonoscope by the physician can cause region 12 of the colonoscope to bear against and cause displacement of the rectosigmoid junction RJ, as illustrated by dotted lines 12' and RJ' in FIG. 1.

Such distension may result in patient discomfort or spasm, and if unnoticed, could result in injury to the colon. The potential for movement of colonoscope to cause distension, discomfort or spasm is also great where the colonoscope must negotiate left colic flexure LCF and right colic flexure RCF, and results in a large portion of such examinations terminating before the physician can advance distal tip 11 to cecum CE.

The present invention provides apparatus and methods for placing a diagnostic or therapeutic instrument through the tortuous or unpredictably supported anatomy of a hollow body organ, such as the esophagus or colon, while reducing the risk of distending or injuring the organ. Apparatus constructed in accordance with the present invention permits an endoscope or colonoscope to be readily advanced into a patient's tortuous or unsupported anatomy by selectively shape-fixing an overtube portion of the apparatus, while also preventing tissue from being captured or pinched between the overtube and scope.

Figure 2:
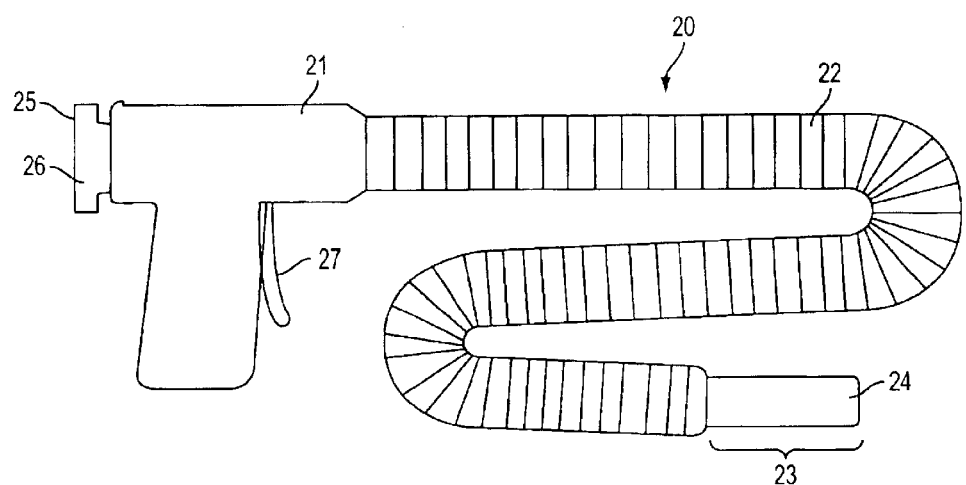
FIG. 2 is a side view of illustrative apparatus of the present invention.

Referring now to FIG. 2, apparatus 20 of the present invention is described. Apparatus 20 comprises handle 21, overtube 22, and distal region 23 having atraumatic tip 24. Handle 21 includes lumen 25 that extends from Toughy-Borst valve 26 through overtube 22, distal region 23 and atraumatic tip 24. Lumen 25 is configured to facilitate passage of a standard commercially available colonoscope, such as colonoscope 10, therethrough. Toughy-Borst valve 26 may be actuated to releasably lock colonoscope 10 to apparatus 20 when colonoscope 10 is inserted within lumen 25. As described hereinafter, overtube 22 is configured so that it can be selectively transitioned between a flexible state and a rigid, shape-fixed state by actuator 27 disposed on handle 21.

Figure 3:
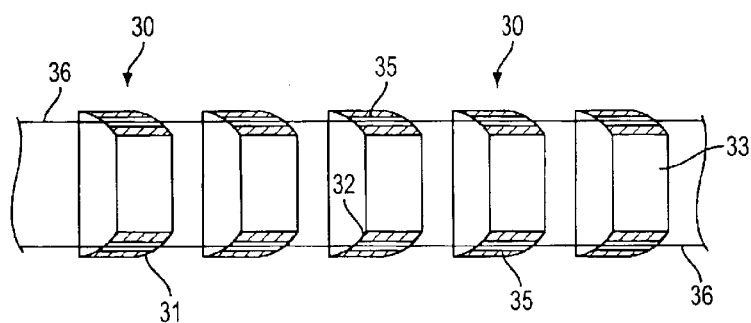
FIG. 3 is a side-sectional exploded view of nestable elements of a first embodiment of an overtube suitable for use in the apparatus of FIG. 2.

In FIG. 3, illustrative embodiment of overtube 22 comprises a multiplicity of nestable elements 30. For purposes of illustration, nestable elements 30 are shown spaced-apart, but it should be understood that elements 30 are disposed so that their adjacent surfaces 31 and 32 coact. Each of nestable elements 30 has central bore 33 to accommodate colonoscope 10, and preferably three or more tension wire bores 35. When assembled as shown in FIG. 2, nestable elements 30 are fastened with adjacent surfaces 31 and 32 disposed in a coacting fashion by a plurality of tension wires 36 that extend through tension wire bores 35.

In a preferred embodiment, adjacent surfaces 31 and 32 of each nestable element 30 are contoured to mate with the next adjacent element, so that when tension wires 33 are relaxed, surfaces 31 and 32 can rotate relative to one another. Tension wires 36 are fixedly connected to the distal end of overtube 22 at the distal ends and to a tensioning mechanism disposed within handle 21 at the proximal ends. When actuated by actuator 27, tension wires 36 impose a load that clamps adjacent surfaces 31 and 32 of nestable elements 30 together at the current relative orientation, thereby fixing the shape of overtube 22.

When the load in tension wires 36 is released, tension wires 36 provides for relative angular movement between nestable elements 30. This in turn renders overtube 22 sufficiently flexible to negotiate a tortuous path through the colon. When the tensioning mechanism is actuated, however, tension wires 36 are retracted proximally to apply a clamping load to the nestable elements. This load prevents further relative movement between adjacent elements 30, and stiffens overtube 22 so that any distally directed force applied to colonoscope 10 causes distal tip 11 to advance further into the colon, rather than cause overtube 22 to bear against the wall of the colon. The shape-fixed overtube absorbs and distributes vector forces, shielding the colon wall.

Figure 4:
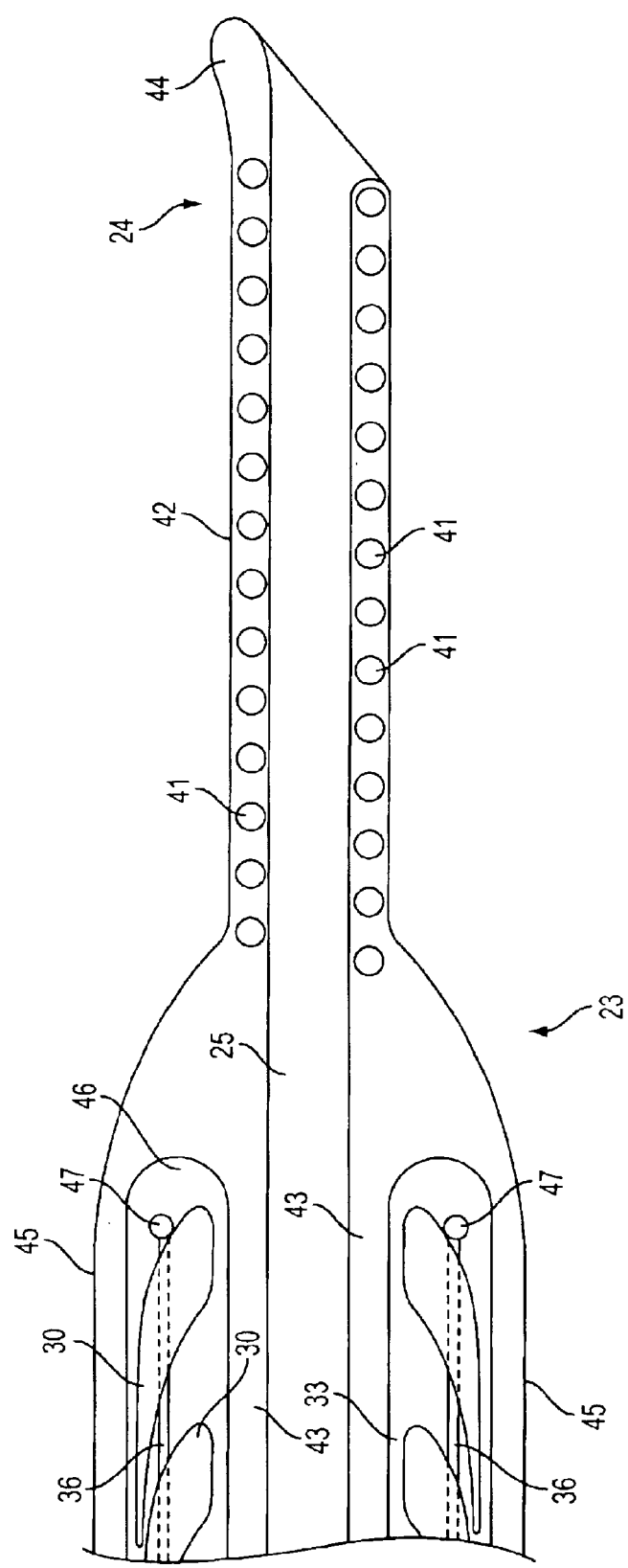
FIG. 4 is a side-sectional view of a distal region of the apparatus of FIG. 2 constructed in accordance with principles of the present invention.

Referring now to FIG. 4, an illustrative embodiment of distal region 23 and atraumatic tip 24 is described. Distal region 23 comprises flexible, kink-resistant coil 41 encapsulated in flexible layer 42. Layer 42 preferably comprises a soft elastomeric and hydrophilic coated material, such as silicon or synthetic rubber, and extends through bores 33 of nestable elements 30 to form liner 43 for lumen 25. Layer 42 extends to handle 21 at the proximal end, and at the distal end terminates in enlarged section 44 that forms atraumatic tip 24.

Layer 42 preferably joins with or is integrally formed with flexible elastomeric cover 45 which encapsulates nestable elements 30 in annular chamber 46. Cover 45 provides a relatively smooth outer surface for overtube 22, and prevents tissue from being captured or pinched during relative rotation of adjacent nestable elements 30.

In accordance with one aspect of the present invention, colonoscope 10 may be positioned with its distal tip 11 disposed in distal region 23, so that deflection of steerable distal tip 11 imparts an angular deflection to distal region 23 and atraumatic tip 24. To ensure that there is no gross relative motion between colonoscope 10 and apparatus 20, Toughy-Borst valve 26 is tightened to engage apparatus 20 to the colonoscope. In this manner, colonoscope 10 and distal region 23 may be simultaneously advanced through the colon, with the distal tip of the colonoscope providing a steering capability to apparatus 20. Apparatus 20 therefore may be advantageously advanced together with colonoscope 10 when overtube 22 is in the flexible state, reducing relative motion between apparatus 20 and colonoscope 10 to those instances where overtube 22 must be shape-locked to prevent distension of the colon.

Still referring to FIG. 4, terminations 47 of tension wires are described. Terminations 47 illustratively comprise balls welded or molded onto the ends of tension wires 36 that ensure the tension wires cannot be pulled through tension wire bores 35 of the distalmost nestable element 30. This ensures that the nestable elements cannot come loose when overtube 22 is disposed within a patient.

Alternatively, terminations 47 may comprise knots formed in the ends of tension wires 36, or any suitable fastener that prevents the tension wires from being drawn through the tension wire bores of the distalmost nestable element. Advantageously, cover 45 provides additional assurance that all of nestable elements 30 can be safely retrieved from a patient's colon in the unlikely event of a tension wire failure.

Figure 5:
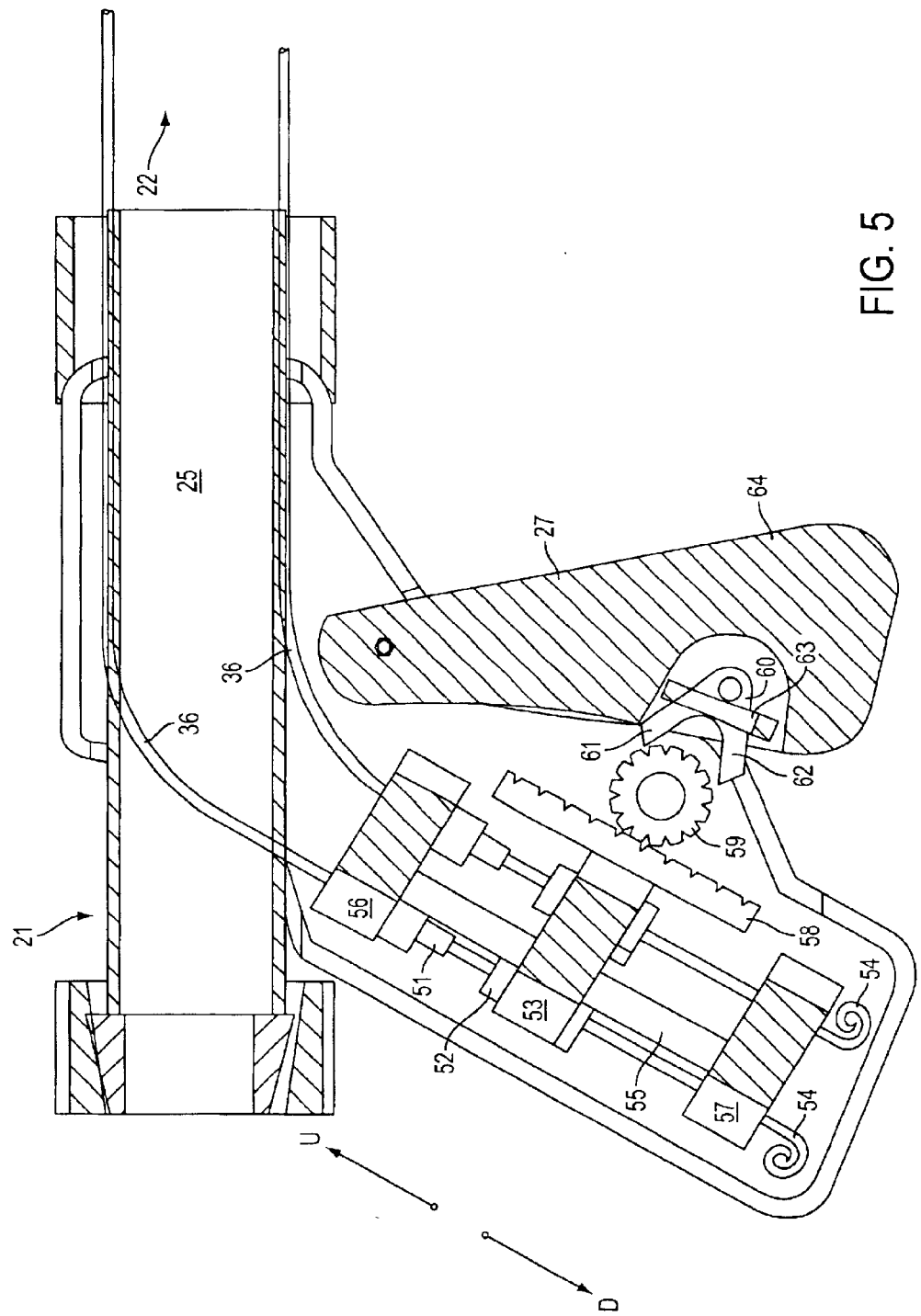
FIG. 5 is a side-sectional view of an illustrative arrangement of a mechanism suitable for use in the handle of the apparatus of FIG. 2.

Referring now to FIGS. 2 and 5, tension wires 36 within overtube 22, liner 43 and lumen 25 extend from distal region 23, through overtube 22, and to handle 21. Within handle 21, each tension wire 36 passes through wire lock release 51 fixedly attached to handle 21, and wire lock 52 disposed on slide block 53. Each tension wire 36 terminates at wire tension spring 54, which maintains tension wires 36 in light tension even when overtube 22 is in the flexible state. The degree of tension provided by wire tension springs 54 is not sufficient to clamp adjacent nestable elements 30 together, but on the other hand does not let gaps form between adjacent nestable elements, and helps to manage the tension wire take up or slack as overtube 22 makes various bends.

Slide block 53 is keyed to slide along rail 55 disposed between limit blocks 56 and 57, and comprises a rigid block having a bore through which rail 55 extends and an additional number of bores as required for the number of tension wires 36 employed. Rack gear 58 is fixedly coupled to slide block 53. Rack 58 mates with pinion gear 59, which is in turn driven by bi-directional pawl 60 coupled to actuator 27. Pinion gear 59 may be selectively engaged by either prong 61 or 62 of bidirectional pawl 60, depending upon the position of selector switch 63.

If prong 61 is selected to be engaged with pinion gear 59, a squeezing action applied to actuator 27, illustratively hand grip 64, causes rack 53 to move in the D direction in FIG. 5, thereby applying tension to tension wires 36. Repeated actuation of hand grip 64 causes slide block 53 to move progressively further in direction D, thereby applying an increasing clamping load on nestable elements 30. Any slack lengths of tension wires 36 extending below slide block 53 are taken up by wire tension springs 54. As discussed in greater detail below with respect to FIG. 6, wire locks 52, which are affixed to slide block 53, engage and retract tension wires 36 concurrently with movement of slide block 53 in the D direction.

If prong 62 is instead chosen by selector switch 63 to engage pinion gear 59, repeated actuation of hand grip 64 causes slide block 53 to translate in direction U, thereby relaxing the tensile load applied by tension wires 36 to nestable elements 30. Repeated actuation of hand grip 64 causes slide block 53 to advance in direction U until wire lock releases 51 engage wire locks 52, releasing all tension from tension wires 36 except that provided by wire tension springs 54. This action permits the clamping forces imposed on nestable elements 30 to be progressively reduced and render overtube 22 progressively move flexible, until when wire lock releases 51 engage wire locks 52, the overtube is returned to its most flexible state.

Figure 6:
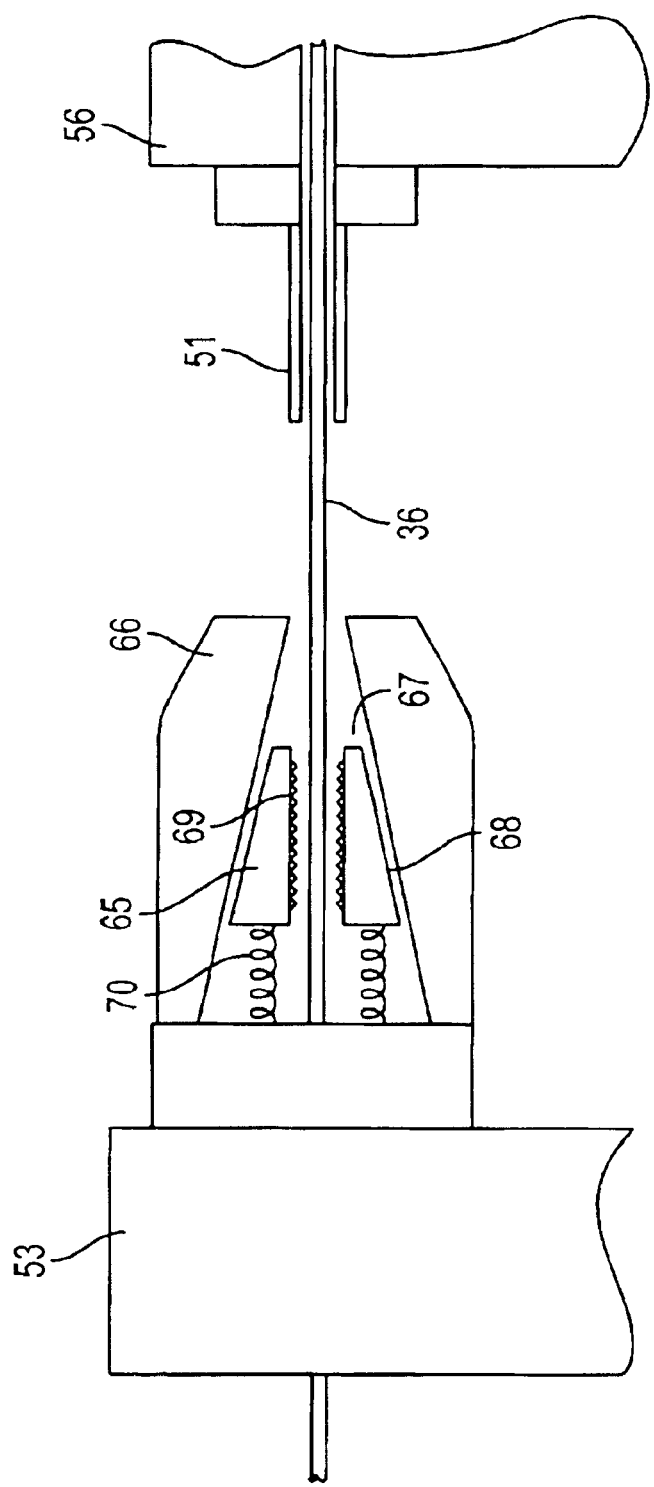
FIG. 6 is a side-sectional view of the detail of a wire clamping system suitable for use in the handle of FIG. 5.

Referring to FIG. 6, wire lock 52 and lock release 51 are described in greater detail. Wire lock 52 includes jaws 65 disposed within collet 66. Collet 66 includes a tapered conical bore 67. Jaws 65 have ramped exterior surfaces 68 and teeth 69, and are biased against the surface formed by the tapered conical bore by springs 70. Teeth 69 are configured to engage tension wire 36 under the bias force of springs 70. When slide block 53 is moved in direction D (see FIG. 5), jaws 65 engage and grasp tension wire 36 and retract the tension wire in direction D.

To disengage teeth 69 from tension wire 36, e.g., when it is desired to allow overtube 22 to return to a flexible state, slide block 53 is actuated as described previously to move in direction U. Further actuation of slide block 53 towards limit block 56 and wire lock release 51 causes wire lock release 51 to extend into tapered conical bore 67 and push jaws 65 backward against the bias of springs 70. Once tension wires 36 are freed from jaws 65, overtube 22 returns to its most flexible state.

Figure 7A:
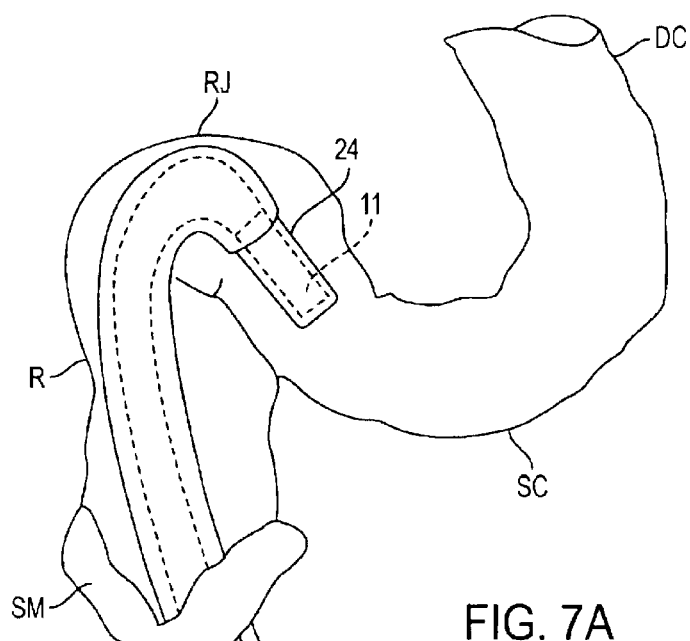
FIGS. 7A–7C are schematic views of a method of using the apparatus of the present invention.
Figure 7B:
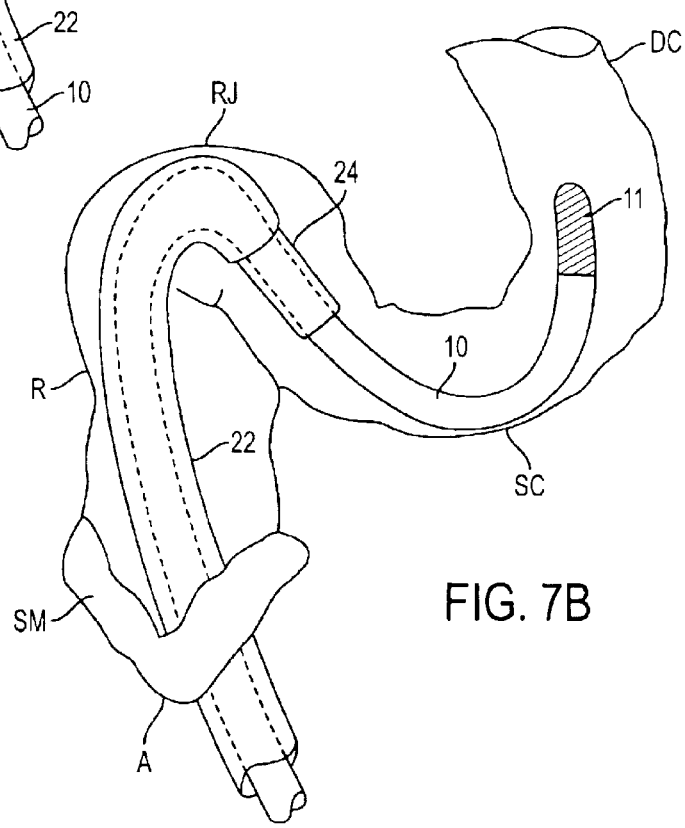
Figure 7C:
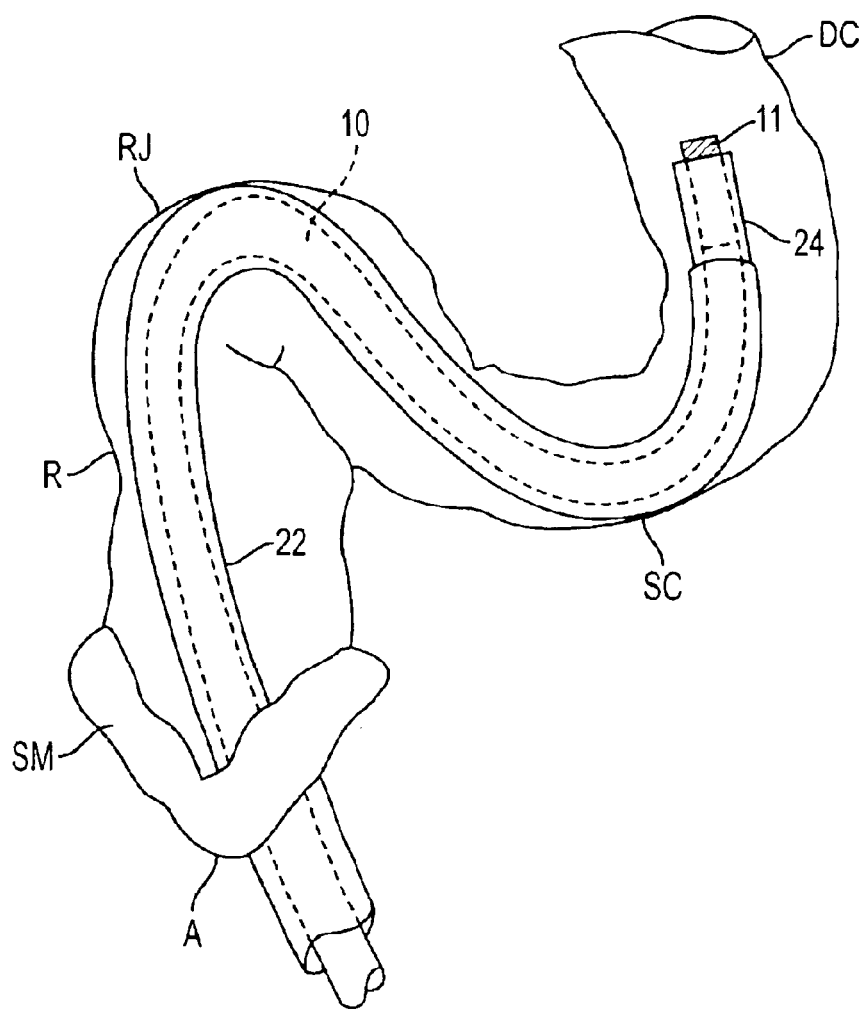

Referring to FIGS. 7A–7C, a method of using apparatus 20 is described. Colonoscope 10 and overtube 22 may be inserted into the patient either simultaneously or by first backloading the overtube onto the colonoscope. To perform simultaneous insertion, colonoscope 10 is introduced into lumen 25 of handle 21 until distal tip 11 of the colonoscope is disposed in distal region 23. Toughy-Borst valve 26 is actuated to lock apparatus 20 to colonoscope 10. As one unit, colonoscope 10 and overtube 22 are inserted into rectum R of the patient, and navigated about rectosigmoid junction RJ. As discussed previously, steerable distal tip 11 may be used to impart angular deflection to flexible tip 24 to steer tip 24 about tortuous curves, such as rectosigmoid junction RJ. Once distal tip 11 and tip 24 have been negotiated past rectosigmoid junction RJ, the current shape of overtube 22 is locked in the manner discussed above to provide a rigid channel through which colonoscope 10 may be further advanced into the colon without distending rectosigmoid junction RJ. Once distal tip 11 of colonoscope 10 is negotiated past sigmoid colon SC, overtube 22 is released from its rigid state and advanced along colonoscope 10 until it too traverses sigmoid colon SC. Again, the current shape of overtube 22 is locked to provide a rigid channel for advancement of colonoscope 10. To negotiate the remainder of the colon, such as left colic flexure LCF and right colic flexure RCF, the preceding steps may be repeated. In this manner, colonoscope 10 and overtube 22 may be navigated through the tortuous curves of the colon without distending the colon, and thereby causing discomfort, spasm or injury.

Figure 8:
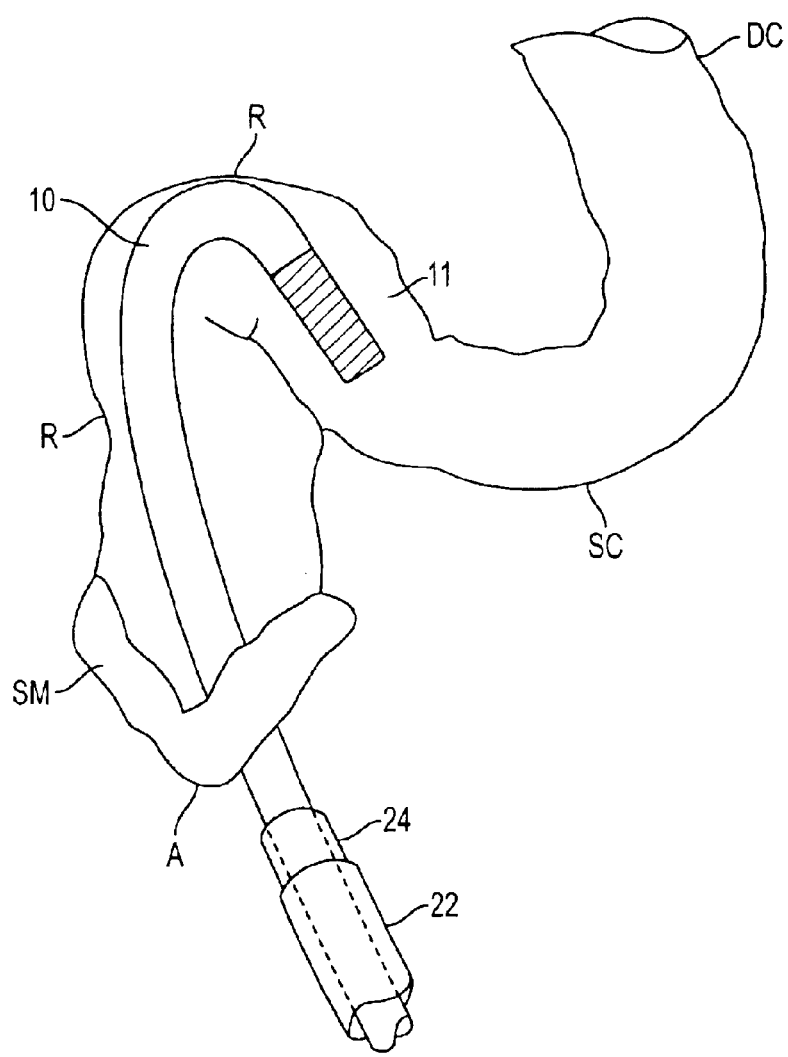
FIG. 8 is a schematic view of an alternative step in the method of using the apparatus of the present invention.

Alternatively, rather than simultaneously inserting both colonoscope 10 and overtube 22 into the patient, apparatus 20 first may be backloaded onto the colonoscope. First, overtube 22 is threaded onto colonoscope 10 and positioned proximal distal tip 11, as shown in FIG. 8. Colonoscope 10 then is inserted into rectum R of the patient and advanced around rectosigmoid junction RJ. Overtube 22 is advanced along colonoscope 10 into rectum R of the patient, using colonoscope 10 as a guide rail to negotiate rectosigmoid junction RJ. Once overtube 22 traverses rectosigmoid junction RJ to the position shown in FIG. 7A, the shape of overtube 22 is locked to provide a rigid channel through which colonoscope 10 may be further advanced into the colon. To negotiate the remainder of the colon, the steps discussed in reference to FIGS. 7B–7C may be performed.

Figure 9:
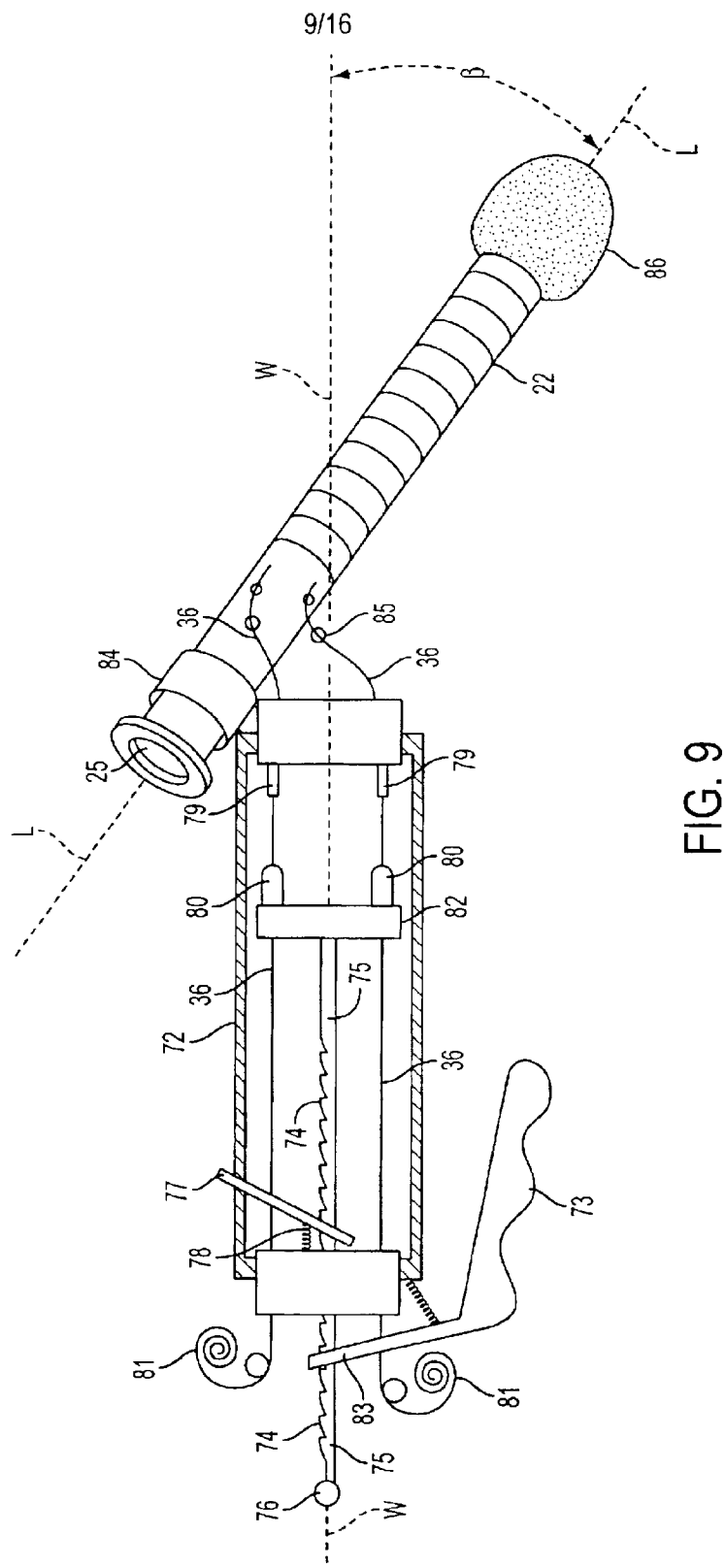
FIG. 9 is a side view of an alternative embodiment of the apparatus of the present invention.

With respect to FIG. 9, an alternative embodiment of handle 21 is described. Like handle 21 of FIG. 5, handle 71 also embodies a ratchet-type tension mechanism, but in this embodiment overtube 22 may be separated from handle 71, thereby permitting handle 71 to be sterilized for repeated use. Handle 71 comprises housing 72 having actuator 73 that engages teeth 74 disposed along the length of rod 75, which defines working axis W of handle 71. Push knob 76 is affixed to the proximal end of rod 75 so that when pawl 77 is released, rod 75 may be pushed in a distal direction. Pawl 77 engages teeth 74 of rod 75 to prevent distally-directed motion of rod 75. Spring 78 biases pawl 77 against teeth 74 of rod 75, to provide a one-way ratchet effect when actuator 73 is squeezed.

As in the embodiment of FIG. 5, tension wires 36 extend through wire lock releases 79, wire locks 80, and are coupled to wire tension springs 81. Wire locks 80 are affixed to block 82, which translates within housing 72 responsive to movement of rod 75. Wire locks 80 and wire lock releases 79 operate in the same manner as described with reference to FIG. 6.

In operation, squeezing actuator 73, illustratively a hand grip, causes fork 83 to move rod 75 in a proximal direction so that pawl 77 captures the next distalmost tooth 74. This movement also causes wire locks 80 to engage and grasp tension wires 36 and retract the tension wires proximally. Further actuation of actuator 73 causes overtube 22 to stiffen in the manner previously described. Spring 78 retains pawl 77 in continuous engagement with teeth 74, thereby preventing rod 75 from moving in the distal direction.

When it is desired to make overtube 22 more flexible, pawl 77 is released and knob 76 pushed in the distal direction so that wire locks 80 engage wire lock releases 79. As described above, this releases tension wires 36 from wire locks 80 and permits overtube to assume its most flexible state.

In accordance with one aspect of the present invention, overtube 22 of the embodiment of FIG. 9 may be replaceably removed from yoke 84 of handle 71. In addition tension wires 36 further may comprise connectors 85 that permit the tension wires to be disconnected. Such a configuration permits the overtube to be removed and discarded after a single use, while the handle may be sterilized and reused.

Yoke 84 is also configured to position overtube 22 so that longitudinal axis L of the overtube is angularly displaced from working axis W by a predetermined angle β. This arrangement prevents handle 71 from interfering with advancement of colonoscope 10 into lumen 25.

In accordance with yet another aspect of the present invention, overtube 22 includes atraumatic tip 86 that comprises a soft foam-like material. Atraumatic tip 86 not only facilitates advancement of overtube 22 in traversing tortuous anatomy, but also serves to retain the organ wall a safe distance away from the opening through which the colonoscope is reciprocated by radially expanding the organ wall in the vicinity of the tip, as described hereinbelow with respect to FIG. 14A. Accordingly, atraumatic tip 86 reduces the potential for tissue to be caught or pinched in lumen 25 when the colonoscope is manipulated.

With respect to FIGS. 10A and 10B, an alternative structure is described to facilitate movement of a colonoscope within lumen 25 of overtube 22. In particular, instead of using inner lining 43 as depicted in FIG. 4, some or all of nestable elements 30 may include roller bearings 87 that are received in insets 89 formed in nestable elements 30. Bearings 87 may be disposed on ring 88 to facilitate assembly of the device.

FIGS. 11A and 11B depict a further alternative embodiment, in which lubricious flexible rails 90 are disposed within bore 33 of nestable elements 30. Rails 90 span the length of lumen 25, and reduce contact between the colonoscope and the interior of the overtube, thereby facilitating movement of the colonoscope through overtube 22.

Figure 12:
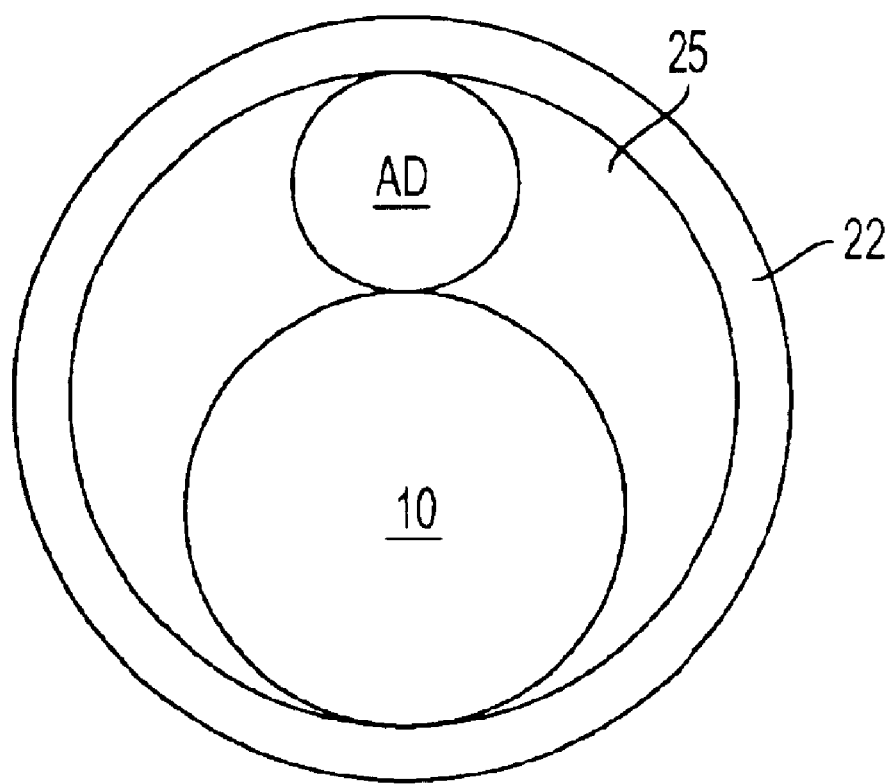
FIG. 12 is a schematic view of the lumen of the overtube of the present invention depicting the use of multiple devices.

In accordance with another aspect of the present invention, the diameter of lumen 25 preferably is configured to facilitate simultaneous passage of more than one diagnostic or therapeutic instrument therethrough. As shown in FIG. 12, lumen 25 may be dimensioned to permit auxiliary devices AD, such as for aspiration, biopsy, or additional lighting, to be advanced alongside colonoscope 10. For example, if lumen 25 has a diameter of 13 mm and colonoscope 10 has an outer diameter of 10 mm, auxiliary device AD, such as a catheter, having a diameter of between 3 F to 9 F may be advanced through the remaining space within lumen 25. Advantageously, this permits auxiliary devices AD to be successively placed within the patient's colon to perform additional diagnostic or therapeutic procedures without the need to remove colonoscope 10 and overtube 22 therefrom.

Figure 13:
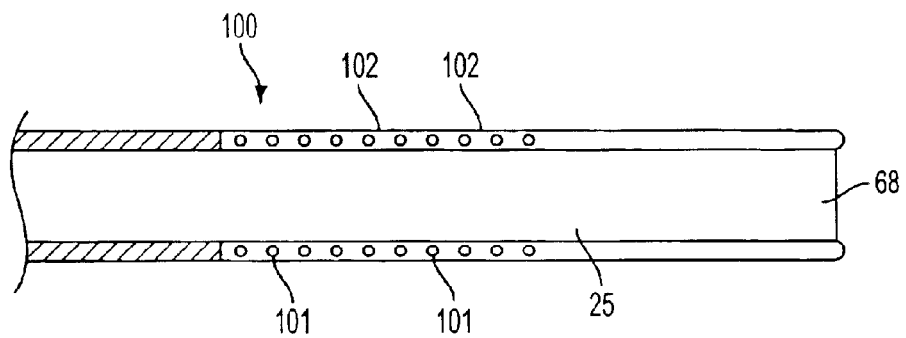
FIGS. 13–18 depict side-sectional views of various alternative embodiments of an atraumatic tip constructed in accordance with the present invention.

Referring to FIG. 13, an alternative embodiment of a distal region suitable for use in the overtube of the present invention is described. Distal region 100 is similar in construction to distal region 23 of the embodiment of FIG. 4, but has flexible coil 101 embedded in only the proximal portion of elastomeric layer 102. Atraumatic tip 102 at the distal end of distal region 24 may further enhance the steerability of the overtube 22 when the steerable tip of the colonoscope is disposed therein.

FIGS. 14–18 illustrate additional configurations of atraumatic tips suitable for causing "tenting" of the wall of the hollow body organ. As used herein, tenting refers to the tendency of the atraumatic tip to be deflected radially outward in the vicinity of the tip of the overtube. This reduces the risk that the wall of the organ will become pinched or caught between the colonoscope and the entry to overtube 22 when the colonoscope is retracted within the overtube.

Figure 14A:
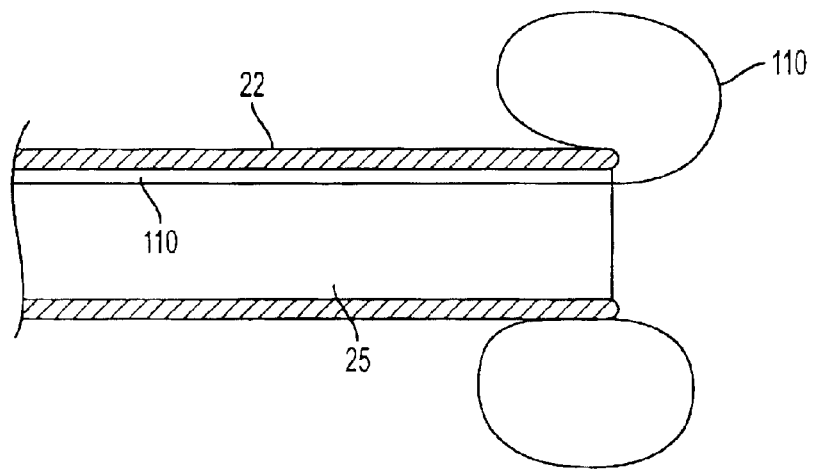
Figure 14B:
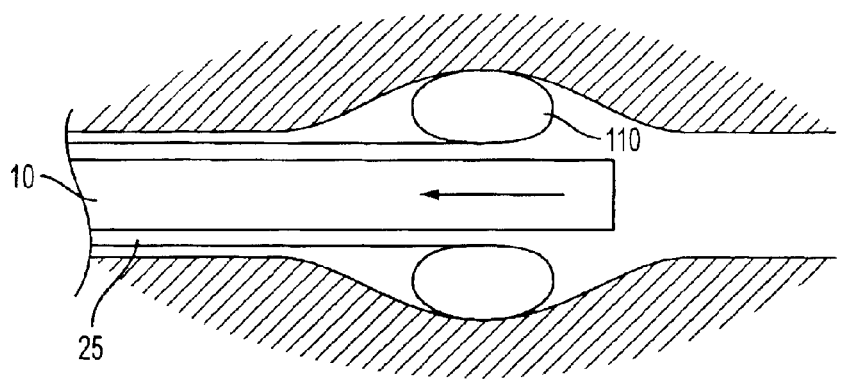

FIG. 14A shows atraumatic tip 24 in the form of an inflatable donut-shaped balloon 110 affixed to distal region 23 of overtube 22. Inflation lumen 111 extends from the handle through overtube 22 to provide fluid communication between balloon 110 and an inflation source, such as a syringe (not shown). As illustrated in FIG. 14B, when balloon 110 is inflated, the wall of the colon radially deflects around balloon 110. Thus, when colonoscope 10 is retracted into lumen 25, it is less likely that the wall of the colon will be pinched or potentially dissected between overtube 22 and colonoscope 10.

Figure 15:
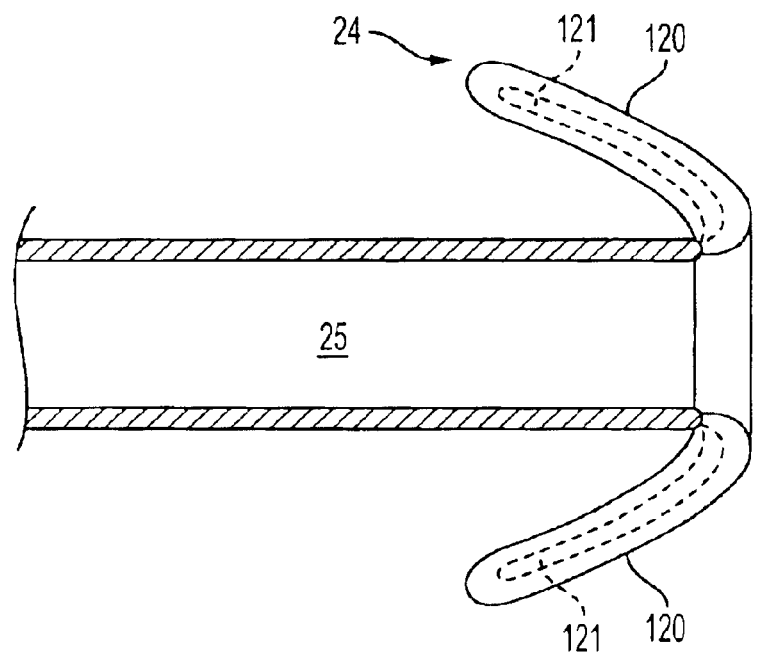

FIG. 15 depicts a further alternative embodiment of atraumatic tip 24, comprising soft membrane 120 covering shape memory alloy petals 121. Petals 121 preferably comprise loops of shape memory alloy wire, e.g., nickel titanium alloy, and extend radially outward in the proximal direction near the distal opening into lumen 25, so that the proximal end of membrane-covered petals causes the "tenting" effect described hereinabove. The shape memory alloy may be activated to adopt a pre-formed shape when exposed to body temperature, and returned to a contracted state by flushing overtube 22 with cold water or air. Alternatively, petals 121 may be mechanically extended or retracted, or self-expanding.

Figure 16:
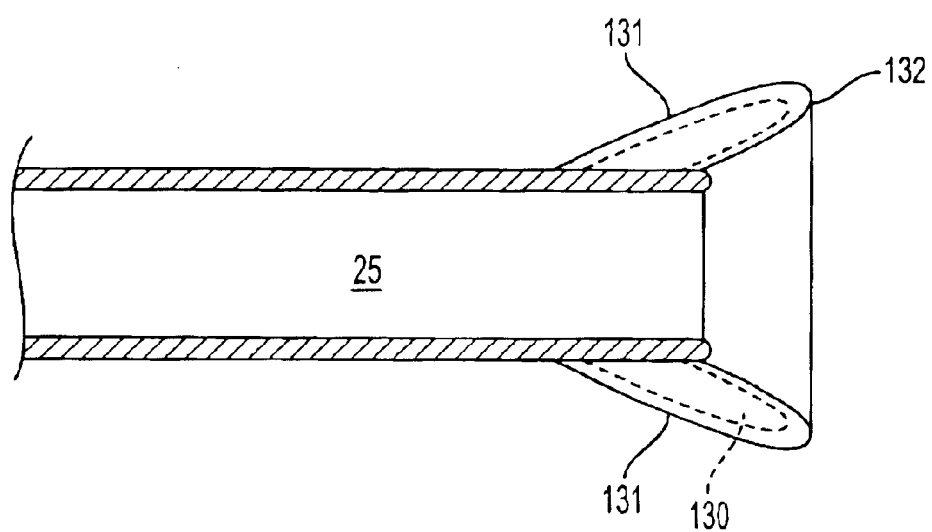

FIG. 16 depicts a further alternative embodiment of atraumatic tip 24. In the embodiment of FIG. 16, petals 130 covered by soft elastomeric membrane 131 extend distally from distal region 23 to form funnel-shaped element 132. Atraumatic tip 24 provides a similar tenting effect to that described for the preceding embodiments.

Figure 17:
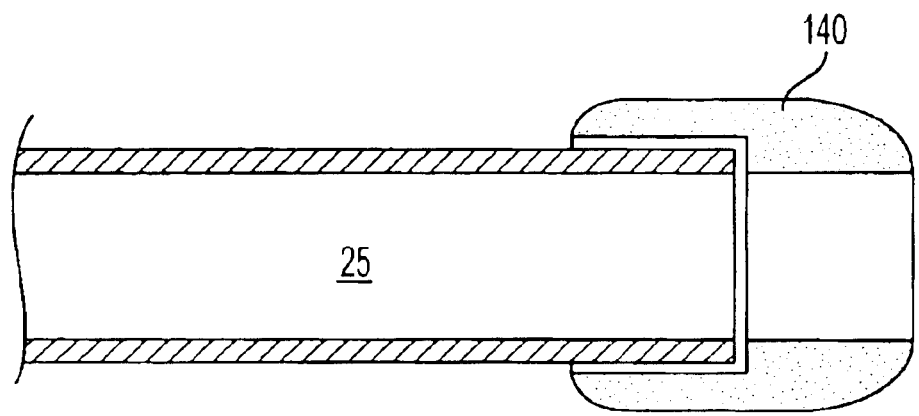
Figure 18:
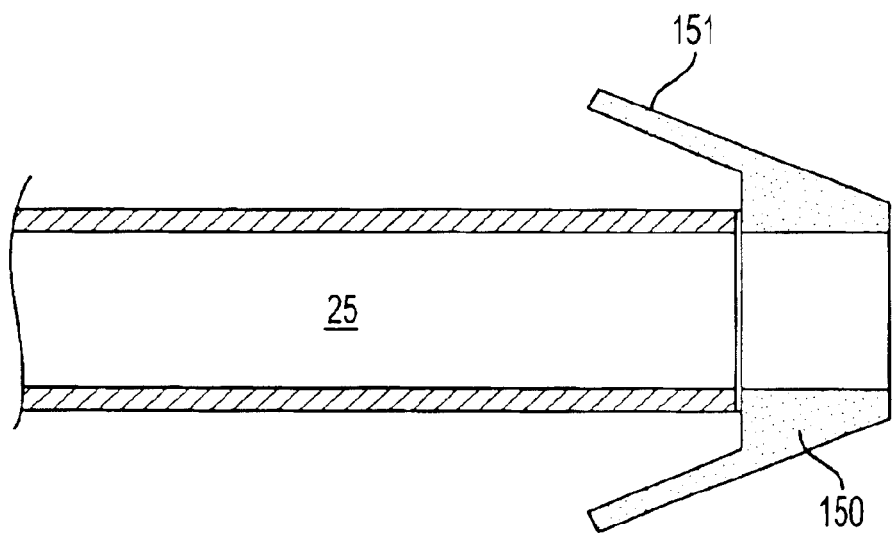

FIGS. 17–18 provide further alternative configurations for atraumatic tip 86 of the embodiment of FIG. 9. Tip 140 preferably comprises a foam or soft elastomer, and may be affixed to distal region 23 of overtube 22 using a suitable biocompatible adhesive. FIG. 18 depicts an alternative shape for a foam or soft elastomer bumper 150, which includes a proximally-extending flange 151. Of course, one of ordinary skill in the art will recognize that other configurations may be used in accordance with the principles of the present invention to form atraumatic tips that cause localized tenting of the colon wall, and these atraumatic tips may be used with the passively-steerable distal regions of the embodiments of FIGS. 4 and 13.

With respect to FIGS. 19–23, alternative embodiments of overtube 22 are described. Unlike overtube 22 of the above-described embodiments, which comprised a multiplicity of nestable elements that are clamped with a plurality of tension wires, the embodiments of FIGS. 19–23 use alternative clamping mechanisms. In particular, the following embodiments comprise a plurality of links that may be stiffened by the use of compressive sleeves that compress individual links disposed along the length of the overtube.

Figure 19A:
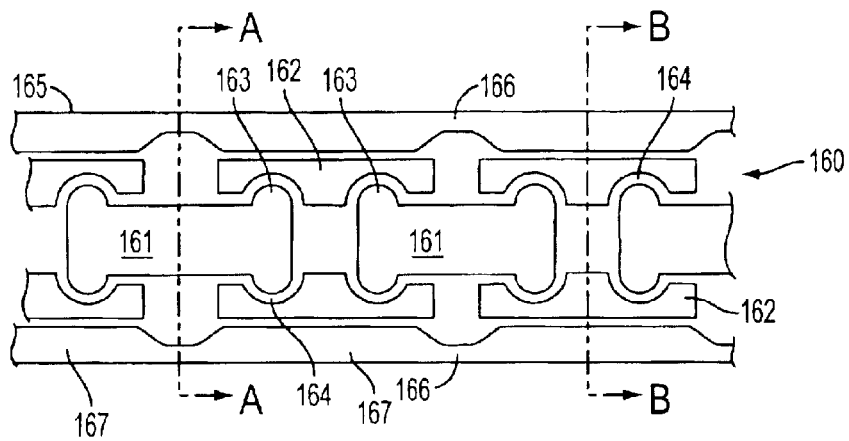
FIGS. 19A–19C are, respectively, a side-sectional view of an alternative embodiment of an overtube suitable for use in the present invention having a multiplicity of interconnected links surrounded by a clamping sleeve, and cross-sectional views of portions of the sleeve.
Figure 19B:
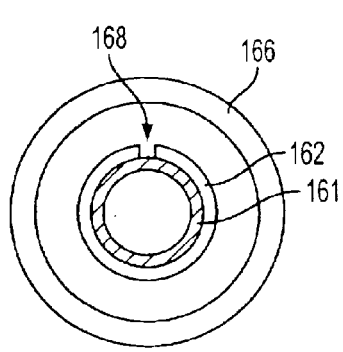
Figure 19C:
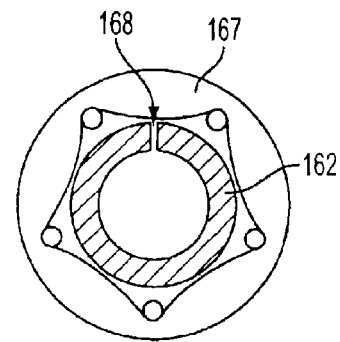

Referring now to FIGS. 19A–19C, a first alternative embodiment of the overtube of the present invention is described. Overtube 160 comprises a multiplicity of alternating spool links 161 and clamp links 162. Each spool link 161 and clamp link 162 has a bore disposed therethrough to accommodate a standard colonoscope. Spool link 161 comprises rounded edges 163 disposed on its distal and proximal ends that are contoured to permit limited rotatable engagement with one of two contoured grooves 164 disposed within the bore of clamp link 162. Accordingly, clamp link 162 comprises a greater outer diameter than spool link 161. Each clamp link 162 also has through-wall split 168 longitudinally disposed to permit a reduction in the diameter of clamp link 162 when the clamp link is compressed, as discussed hereinafter.

Still referring to FIGS. 19A–19C, a first embodiment of a compressive sleeve comprising inflatable sleeve 165 having first compressive portions 166 and second compressive portions 167. Sleeve 165 is configured so that the inner diameters of second compressive portions 167 are smaller than those of first compressive portions 166 when sleeve 165 is inflated. Second compressive portions 167 may be disposed to engage clamp links 162. Thus, when inflatable sleeve 165 is inflated by an inflation source (not shown) coupled to the handle, second compressive portions 167 compress against clamp links 162 to shape-fix overtube 160. In FIGS. 19B and 19C, cross sectional views of first compressive portions 166 and second compressive portions 167, respectively, are shown when sleeve 160 is in its inflated state.

Figure 20:
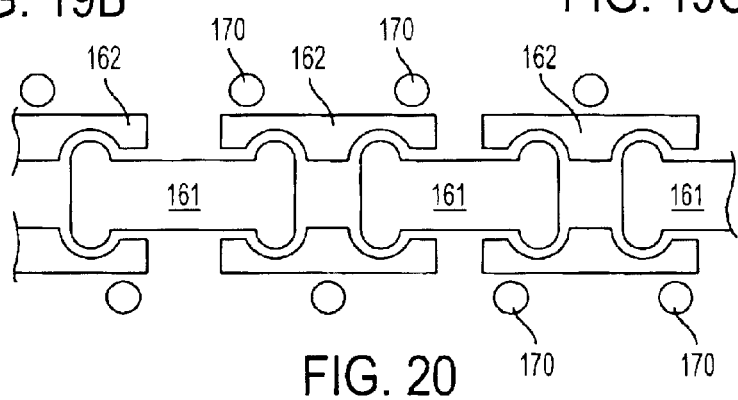
FIG. 20 is a side-sectional view of a further alternative embodiment of an overtube constructed in accordance with the present invention having a spiral bladder to actuate the clamping links.

FIG. 20 illustrates an alternative embodiment of a compressive sleeve that also comprises an inflatable bladder. Unlike inflatable bladder 160 of FIGS. 19A–19C, spiral bladder 170 has a constant inner diameter. Spiral bladder 170 preferably is helically disposed around the overtube. Accordingly, when bladder 170 is inflated, clamp links 162 are compressed onto spool links 161 to stiffen the overtube.

Figure 21:
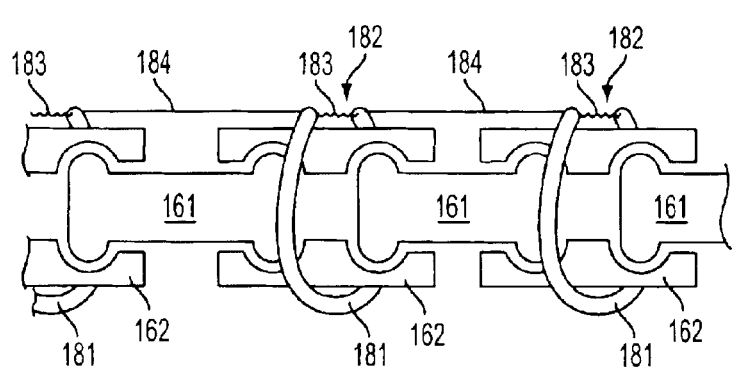
FIG. 21 is a side-sectional view of another alternative embodiment of an overtube of the present invention having thermally-actuable bands.

FIG. 21 depicts a further embodiment of a compressive sleeve 180, comprising discontinuous hoops 181 made of shape memory alloy (e.g. nickel titanium alloy). Each hoop 181 includes gap 182, which is spanned by spring 183. Each hoop 181 is electrically connected to neighboring hoops 181 via insulated wires 184, so that a serial electrical circuit is established. When hoops 181 are energized, they undergo a phase transition that causes the hoops to contract into a preformed shape that is diametrically smaller than the non-energized shape. Since hoops 181 may be disposed about clamp links 162, contraction of hoops 181 may be used to apply a clamping load that compresses links 162 onto spool links 161 to stiffen the overtube.

Springs 183 contribute to structural integrity when hoops 181 are in their non-energized state. To energize and thereby contract hoops 181, an electrical current may be run through wires 184. To return hoops 181 to their non-contracted state and thereby return the overtube 22 to its flexible state, hoops 181 may be flushed with cold water or air. Of course one of ordinary skill in the art will recognize that hoops 181 also may be individually energized, thus requiring a parallel circuit.

Figure 22A:
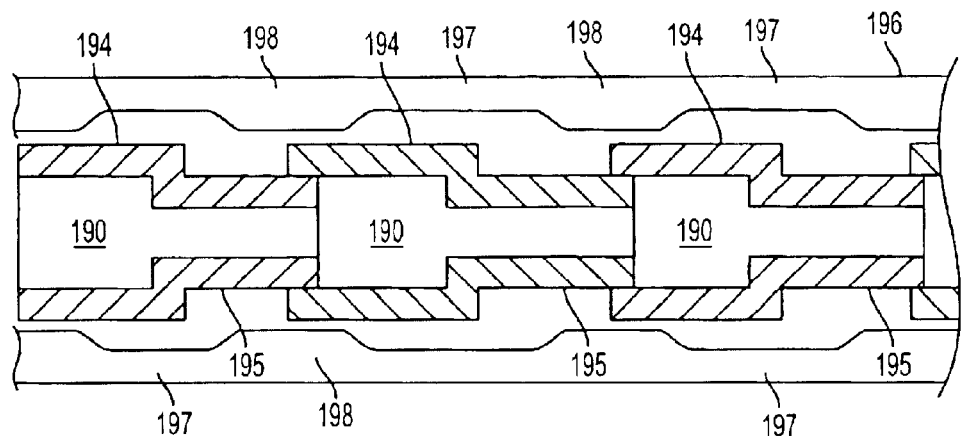
FIGS. 22A and 22B are side-sectional views of a yet further alternative embodiment of an overtube of the present invention comprising a series of helical links having regions of different durometer.
Figure 22B:
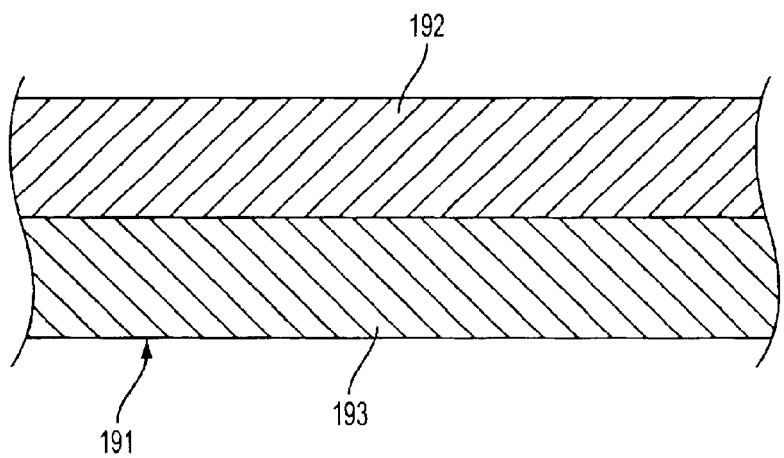

With respect to FIGS. 22A–22B, a still further alternative embodiment of an overtube suitable for use in the present invention is described. This embodiment comprises helical links 190 that are formed from an integral strip 191 having regions of different durometer, e.g., rigid material 192 and soft material 193. When strip 191 is helically wound, helical links 190 are formed having rigid portions 194 and soft portions 195. Rigid portions 194 provide structural integrity to the overtube, while soft portions 195 provide flexibility.

Helical links 190 are disposed within compressive sleeve 196, which includes first compressive portions 197 and second compressive portions 198. Compressive sleeve 196 is identical in structure and operation to that described in FIGS. 19A–19C, except that second compressive portions 198 are aligned with, and apply a clamping force to, rigid portions 194 of helical links 190. It will of course be understood that an overtube in accordance with the principles of the present invention could alternatively be formed using helical links 190 and either of the clamping systems described with respect to FIGS. 20 and 21.

Figure 23:
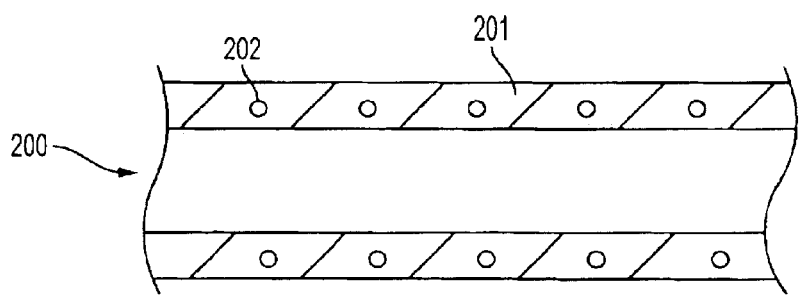
FIG. 23 is a side-sectional view of yet another alternative embodiment of an overtube having thermally regulated stiffness.

With respect to FIG. 23, a still further embodiment of an overtube suitable for use in the apparatus of the present invention is described. Overtube 200 comprises a heat-softenable polymer layer 201, (e.g., Carbothane®, a proprietary urethane-based polymer available from Thermedics Polymer Products, Woburn, Mass.), having wire 202 embedded within it. Wire 202 is coupled at the handle to an energy source, so that by passing an electric current through wire 202, sufficient resistive heating occurs to soften the polymer layer 201, rendering it sufficiently flexible to negotiate tortuous or unsupported anatomy. When electrical energy is not supplied to wire 202, no resistive heating of the wire or the polymer layer occurs, and the overtube instead cools and stiffens. Wire 202 serves the dual purpose of providing kink resistance and electric heating.

Still referring to FIG. 23, yet another alternative embodiment of an overtube suitable for use in the present invention comprises a soft elastomeric polymer layer 201 having a shape memory alloy wire 202 embedded within layer 201. In this embodiment, the shape memory alloy is selected to have a martensite transition temperature above body temperature. When wire 202 is heated to a temperature above body temperature, such as by passing an electric current through it, the wire transitions into the austenitic phase, and becomes stiffer, thereby shape locking the overtube. When application of the electric current ceases, wire 202 cools back into the martensitic phase, and renders the overtube flexible.

While preferred illustrative embodiments of the invention are described above, it will be apparent to one skilled in the art that various changes and modifications may be made therein without departing from the invention. The appended claims are intended to cover all such changes and modifications that fall within the true spirit and scope of the invention.

What is claimed is:

1. Apparatus for advancing a first diagnostic or therapeutic instrument having a steerable distal tip into a hollow body organ of unsupported anatomy, the apparatus comprising:
   a handle having a working axis;
   an overtube coupled to the handle, the overtube having an elongated portion, a distal region and a lumen extending therethrough to permit passage of the first diagnostic or therapeutic instrument, the lumen having a longitudinal axis; and
   an atraumatic tip disposed on the distal region,
   wherein the longitudinal axis of the lumen is angled relative to the working axis of the handle where the overtube is coupled to the handle.

2. The apparatus of claim 1 wherein the overtube includes means for locking the overtube in a bent configuration.

3. The apparatus of claim 2 wherein the means for locking the overtube in a bent configuration comprises:
   a plurality of nestable elements;
   a plurality of tension wires that thread the nested elements together; and
   a tensioning mechanism that may be releasably coupled to the plurality of tension wires and to selectively apply a clamping load to the plurality of nestable elements.

4. The apparatus of claim 3 wherein the tensioning mechanism is a ratchet-type tensioning mechanism.

5. The apparatus of claim 2 wherein the means for locking the overtube in a bent configuration comprises:
   a plurality of links, each link having a bore that defines the lumen of the overtube; and
   means for applying a clamping load to the plurality of links.

6. The apparatus of claim 5 wherein the plurality of links comprise:
   a plurality of spool links, each one of the spool links having rounded distal and proximal ends; and
   a plurality of clamp links, each one of the clamp links interposed between adjacent ones of the plurality of spool links, each one of the clamp links having an interior surface having grooves adapted to engage a distal end of a first adjacent spool link and a proximal end of a second adjacent spool link.

7. The apparatus of claim 5 wherein the plurality of links comprise a multiplicity of helical links formed from a material having variable durometer, each helical link having a rigid portion and a soft portion.

8. The apparatus of claim 5 wherein the means for applying a clamping load comprises an elongate inflatable sleeve disposed to surround the plurality of links.

9. The apparatus of claim 8 wherein the elongate inflatable sleeve comprises a plurality of interconnected annular bladders.

10. The apparatus of claim 8 wherein the elongate inflatable sleeve has a helical shape.

11. The apparatus of claim 5 wherein the means for applying a clamping load comprises:
    a plurality of discontinuous, circular hoops made of a shape memory alloy; and
    a plurality of insulated wires that connect the plurality of hoops to an electrical source.

12. The apparatus of claim 2 wherein the means for locking the overtube in a bent configuration comprises a heat-softenable layer having an embedded wire, wherein an electric current passing through the embedded wire softens the heat-softenable layer.

13. The apparatus of claim 2 wherein the means for locking the overtube in a bent configuration comprises a soft layer having an embedded shape memory alloy wire.

14. The apparatus of claim 1 wherein the atraumatic tip comprises an inflatable donut-shaped balloon.

15. The apparatus of claim 1 wherein the atraumatic tip comprises a wire petal having an elastomeric covering.

16. The apparatus of claim 1 wherein the atraumatic tip comprises a foam or soft elastomer bumper.

17. The apparatus of claim 1 wherein the overtube includes means for facilitating passage of the first diagnostic or therapeutic instrument through the lumen of the overtube.

18. The apparatus of claim 1 wherein the lumen is dimensioned to permit passage of a second diagnostic or therapeutic instrument alongside the first diagnostic or therapeutic instrument.

19. The apparatus of claim 1 wherein the handle is reusable, and the overtube is removably coupled to the handle.

20. A method for advancing a first diagnostic or therapeutic instrument having a steerable distal tip into an unsupported, hollow body organ, the method comprising:
    providing an apparatus having a handle having a working axis, an overtube coupled to the handle, the overtube comprising an elongated portion, a lumen extending therethrough to permit passage of the first diagnostic or therapeutic instrument and a distal region, the lumen having a longitudinal axis, and an atraumatic tip disposed on the distal region;
    inserting the apparatus and the first diagnostic or therapeutic instrument into the unsupported, hollow body organ; and
    advancing the first diagnostic or therapeutic instrument through the lumen at an angle relative to the working axis of the handle where the overtube is coupled to the handle.

21. The method of claim 20 wherein providing an apparatus comprises providing an apparatus wherein the handle is reusable, and the overtube is releasably coupled to the handle, the method further comprising releasing the overtube from the handle and reusing the handle.

22. The method of claim 20 further comprising:
    locking the overtube in a bent configuration; and
    advancing the first diagnostic or therapeutic instrument through the lumen of the overtube in the bent configuration.

23. The method of claim 22 wherein providing an apparatus comprises providing an apparatus wherein the overtube comprises a plurality of nestable elements, and a tensioning mechanism that selectively applies a clamping load to the plurality of nestable elements; and locking the overtube in a bent configuration comprises actuating the tensioning mechanism.

24. The method of claim 22 wherein providing an apparatus comprises providing an apparatus wherein the overtube comprises a plurality of links, each link having a bore that defines the lumen of the overtube, and locking the overtube in a bent configuration comprises applying a clamping load to the plurality of links.

25. The method of claim 24 wherein the overtube further comprises an elongate inflatable sleeve disposed to surround the plurality of links, and applying a clamping load to the plurality of links comprises inflating the elongate inflatable sleeve.

26. The method of claim 24 wherein the overtube further comprises a plurality of discontinuous, circular hoops made of a shape memory alloy, and applying a clamping load to the plurality of links comprises inducing the plurality of discontinuous, circular hoops to undergo a phase transition.

27. The method of claim 22 wherein providing an apparatus comprises providing an apparatus wherein the overtube comprises a heat-softenable layer having an embedded wire, and locking the overtube in a bent configuration comprises terminating a supply of electrical energy to the embedded wire.

28. The method of claim 22 wherein providing an apparatus comprises providing an apparatus wherein the overtube comprises a soft layer having an embedded shape memory alloy wire, and locking the overtube in a bent configuration comprises heating the embedded shape memory alloy wire.

29. The method of claim 20 wherein providing an apparatus comprises providing an apparatus wherein the atraumatic tip comprises an inflatable donut shaped balloon, the method further comprising:
deflecting the unsupported, hollow body organ by inflating the inflatable donut shaped balloon.

30. The method of claim 20 wherein providing an apparatus comprises providing an apparatus wherein the atraumatic tip comprises a wire petal having an elastomeric covering, the method further comprising:
deflecting the unsupported, hollow body organ by extending the wire petal in a radially-outwardly direction.

31. The method of claim 20 wherein providing an apparatus comprises providing an apparatus wherein the atraumatic tip comprises a foam or soft elastomer bumper, the method further comprising:
deflecting the unsupported, hollow body organ by contacting the foam or soft elastomer bumper against the unsupported, hollow body organ.

32. The method of claim 20 wherein providing an apparatus comprises providing an apparatus wherein the lumen is dimensioned to permit passage of a second diagnostic or therapeutic instrument alongside the first diagnostic or therapeutic instrument, the method further comprising:
advancing the second diagnostic or therapeutic instrument alongside the first diagnostic or therapeutic instrument.

* * * * *